United States Patent
Parker

(10) Patent No.: US 9,725,836 B2
(45) Date of Patent: Aug. 8, 2017

(54) CUTTING EYE NEEDLE

(71) Applicant: Douglas "Doug" Parker, Redondo Beach, CA (US)

(72) Inventor: Douglas "Doug" Parker, Redondo Beach, CA (US)

( * ) Notice: Subject to any disclaimer, the term of this patent is extended or adjusted under 35 U.S.C. 154(b) by 144 days.

(21) Appl. No.: 14/022,769

(22) Filed: Sep. 10, 2013

(65) Prior Publication Data

US 2015/0167219 A1   Jun. 18, 2015

(51) Int. Cl.
*D05B 85/00* (2006.01)
*A61B 17/06* (2006.01)
*A61B 17/04* (2006.01)

(52) U.S. Cl.
CPC .......... *D05B 85/00* (2013.01); *A61B 17/0467* (2013.01); *A61B 17/06* (2013.01); *A61B 17/06066* (2013.01); *A61B 2017/06019* (2013.01)

(58) Field of Classification Search
CPC ........ D05B 85/00; D05B 85/02; D05B 85/04; D05B 85/06; D05B 85/08; D05B 85/10; D05B 85/12; D05C 7/04; D04H 18/02; A61B 17/06; A61B 17/3209; A61B 17/0493; A61B 17/0467; A61B 17/06066; A61B 2017/06019
USPC ...... 112/122.1, 125, 222, 224, 292, 295, 89; 223/102, 104; 28/115
See application file for complete search history.

(56) References Cited

U.S. PATENT DOCUMENTS

| | | | | |
|---|---|---|---|---|
| 86,769 A | * | 2/1869 | Marriott | 223/102 |
| 207,648 A | * | 9/1878 | Flather | 112/295 |
| 2,553,877 A | * | 5/1951 | Smith | B31B 1/90 493/334 |
| 2,619,059 A | * | 11/1952 | Rosenfeld | 112/222 |
| 2,781,012 A | * | 2/1957 | Kuhar | 112/292 |
| 3,160,157 A | * | 12/1964 | Chisman | 606/223 |
| 3,322,085 A | * | 5/1967 | Weiss | D05B 85/00 122/222 |
| 3,356,047 A | * | 12/1967 | Short | 112/80.08 |
| 3,812,799 A | * | 5/1974 | Spanel | D05C 15/20 112/80.07 |

(Continued)

FOREIGN PATENT DOCUMENTS

CN           201842962       *   5/2011

OTHER PUBLICATIONS

Yanko Design—Cut Needle, Radhika Seth, http://www.yankodesign.com/2010/10/28/a-sharp-needle-eye/, web page, Oct. 28, 2010, USA.*

(Continued)

*Primary Examiner* — Ismael Izaguirre
(74) *Attorney, Agent, or Firm* — Douglas "Doug" Parker

(57) ABSTRACT

Cutting eye needle comprising an elongated portion, a tip portion, and an eye portion comprising a frictionally engaged cutting edge, with adjacent surfaces (14) and (15) intersecting at edge (17) at an angle that creates a frictionally engaged cutting edge, which threads and sews like a conventional hand sewing needle, which is suitable for cutting one or more threads, in professions including the medical field and surgery, and in needlecraft operations particularly suited to quilting, where ends of thread are cut while located inside the cavities of a quilting project, while simultaneously reducing the probability of skin contact of an operator are disclosed.

2 Claims, 2 Drawing Sheets

(56) References Cited

U.S. PATENT DOCUMENTS

| | | | | |
|---|---|---|---|---|
| 3,920,272 | A | * | 11/1975 | Grimm, Jr. ................ 289/18.1 |
| 4,667,860 | A | * | 5/1987 | Feuerman .............. D05B 87/00 |
| | | | | 223/102 |
| 4,889,529 | A | * | 12/1989 | Haindl ......................... 604/274 |
| 5,215,021 | A | * | 6/1993 | Fuhrmann .................... 112/222 |
| 7,966,955 | B2 | * | 6/2011 | Niizeki .......................... 112/89 |
| 2006/0123690 | A1 | * | 6/2006 | Anderson .............. A01K 83/00 |
| | | | | 43/43.16 |
| 2008/0065155 | A1 | * | 3/2008 | Waeschle ......... A61B 17/06066 |
| | | | | 606/223 |
| 2009/0312480 | A1 | * | 12/2009 | Kohama ............. A61M 5/3286 |
| | | | | 524/494 |

OTHER PUBLICATIONS

Douglas "Doug" Parker, needle_prototypes.pdf (attached), photographic image displaying Cutting Eye Needle prototypes, Jan. 6, 2014, USA.

\* cited by examiner

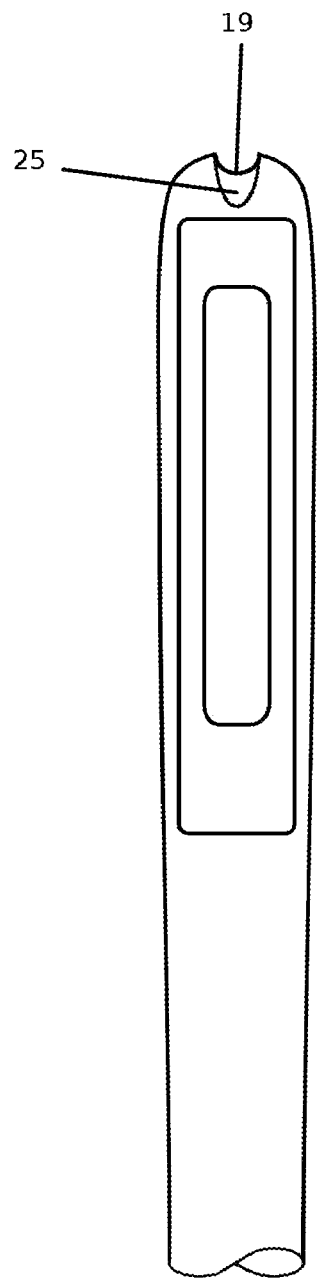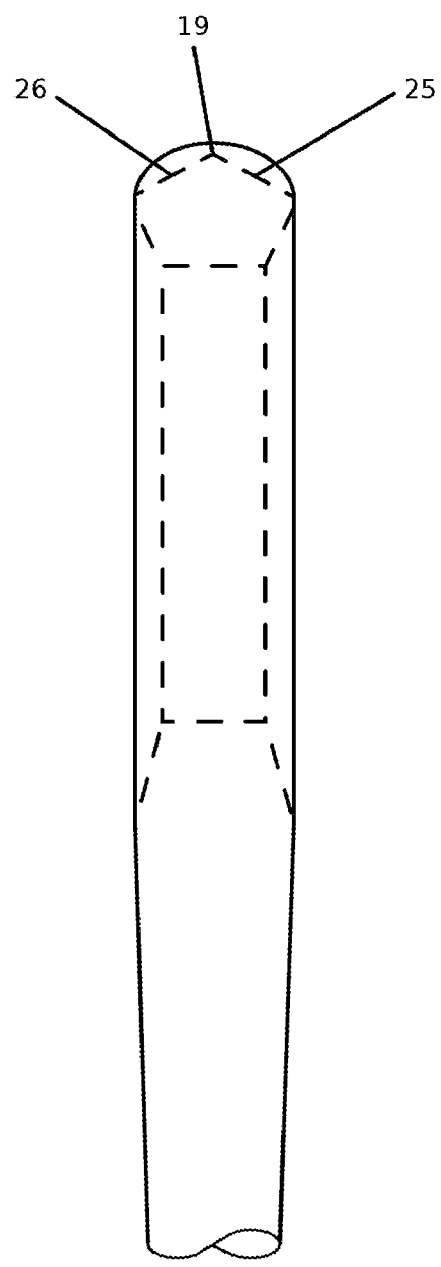
Fig. 2A
Fig. 2B

CUTTING EYE NEEDLE

CROSS-REFERENCE TO RELATED APPLICATIONS

This application claims the benefit of provisional patent application for Ser. No. 61/699692, filed 2012 Sep. 11 by the present inventor.

FEDERALLY SPONSORED RESEARCH

Not Applicable

SEQUENCE LISTING OR PROGRAM

Not Applicable

BACKGROUND OF THE INVENTION

Field of the Invention

The present invention relates generally to a sewing needle. More specifically, the invention is a sewing needle that incorporates an eye portion comprising a cutting edge.

Prior Art

A quilter quilting a project by hand or by machine will use a number of lengths of thread to sew the project together. When the end of a length of thread becomes too short to continue sewing, the quilter will be left with a tail end of thread visible on a front face (here also called a backing) or a back backing of the project. It is desirable for the quilter to hide the tails of thread between the front and back backings of the project.

Using a standard, hand sewing needle, quilters may hide the tail ends of a thread on a quilting project in a number of ways. One manner is to first push a standard needle on its final stitch through a single backing so that the needle is embedded in the space between the two backings. The needle is pushed slightly forward, and again pushed through a backing some distance away from its previous penetration point. This establishes a length of a tail of thread that is hidden between both backings between two penetration points of the needle and the continuation of that length of thread beyond the second penetration point of the needle. By tensioning the thread slightly and sliding the exit point of the needle along the thread toward the previous penetration point of the needle, the backing material is gathered to expose the previously hidden length, now visible outside the final penetration point of the needle and facilitated by the gathering operation. Next, using scissors the quilter can cut the exposed thread close to the desired length. Finally by smoothing out the previously gathered material, the tail of thread is slowly retracted into the space between the backings, backwards through the final penetration point, leaving it hidden between both backings.

The process of hiding the tail end of the thread requires the use of a standard sewing needle or an open eye needle to perform a similar gather-and cut-procedure, and requires scissors or some cutting device to cut the thread. The gathering process also wrinkles the backings of the quilt.

Objects and Advantages

Turning to the injection molding manufacturing process, the process is established and well-known. The metal injection molding process and the production of sintered parts from "green" bodies is well known in the prior art. Generally the green body is formed by filling a die with a powder/binder mixture and compacting the mixture under pressure. The green body, which is a self-supporting structure, is then removed from the die and sintered. During the sintering process, the binder is volatilized and burned out.

Injection molding is a preferred process for manufacturing near-net shape parts from metal and ceramic powders. The tools for producing injection molded parts are generally made from metals such as tool steel and stainless steels due to the high pressures and temperatures normally required for metal and ceramic feedstock materials. Conventional manufacture of needles through traditional stamping processes produces ineffective cutting surfaces within the needle eye.

Injection molding fixtures, which are well known in the art, are designed to interchangeably accept different tool inserts and to be attached to injection molding machines, thus providing highly cost effective production of near-net shape metal, ceramic and plastic parts in high volume.

Accordingly, besides the objects and disadvantages of the needle described in my above patent, several objects and advantages of the present invention are:

(a) to provide a needle which can alternately be a cutting device; and (b) to provide a needle whose cutting edge is designed to reduce the probability of the operator's skin coming in contact with it.

Further objects and advantages are to provide a needle which functions like a conventional hand sewing needle, which cuts one or more threaded threads or non-threaded threads at a time, which simplifies the thread cutting and hiding process for quilters, and does so without wrinkling the backings of the quilting project. Further, to provide quilters easy, controlled access to difficult-to-access, enclosed cavities between backings of a quilting project, and to provide a needle which does not snag. The needle is also easy to manufacture and has little to insignificant unit increase in its manufacturing cost.

Further objects and advantages of my invention will become apparent from a consideration of the drawings and ensuing description.

SUMMARY OF THE INVENTION

In accordance with the present invention a needle comprises an elongated portion, a tip portion that is located adjacent the elongated portion, and an eye portion adjacent the elongated portion and opposite the tip portion having a cutting edge.

The present invention includes a process of manufacture involving injection molding. The injection molding machines which may be employed generally are those found in commercial polymer processing plants.

In the drawings, closely related figures have the same number but different alphabetic suffixes.

DRAWINGS

Figures

FIGS. 2A and 2B show front and side illustrations of a segment of a needle illustrating the eye portion of the needle with a cutting edge in a recessed area on the eye portion of the needle.

Figure 1A:
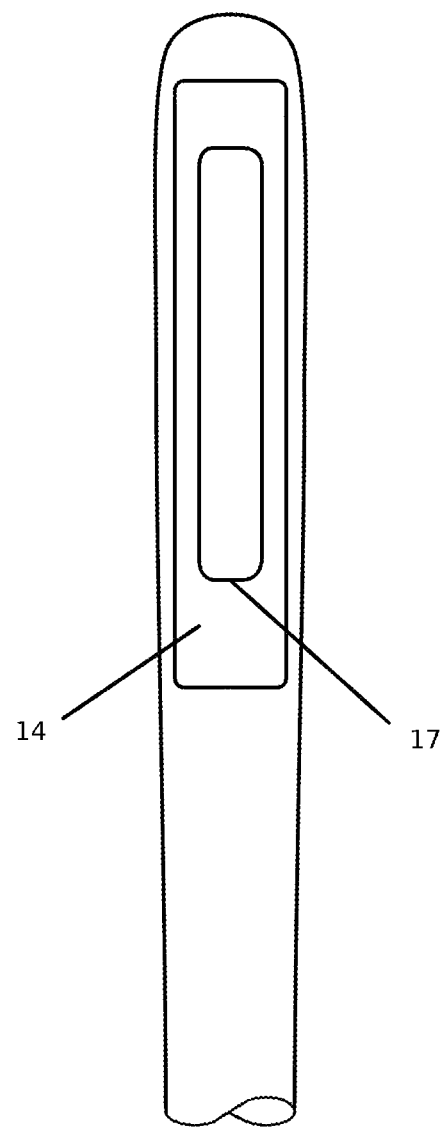
FIGS. 1A and 1B show front and side illustrations of a segment of a needle illustrating the eye portion of the needle with its cutting edge in the eye portion of the needle.

| DRAWINGS - REFERENCE NUMERALS | |
| --- | --- |
| 14 surface | 15 surface |
| 17 edge | 19 edge |
| 25 surface | 26 surface |

DETAILED DESCRIPTION

FIGS. 1A AND 1B

Preferred Embodiment

A preferred embodiment of a needle of the present invention is illustrated in FIGS. 1A (front view) and 1B (side view). The needle has a conventional elongated portion (not shown), a conventional tip portion (not shown) adjacent the elongated portion, and an eye portion adjacent the elongated portion opposite its tip portion, with adjacent surfaces 14 and 15 intersecting at edge 17 at an angle that creates a cutting edge.

Operation

Preferred Embodiment

Manufacturing of the needle of the present invention involves the process of injection molding which is commonly known to anyone skilled in the field. The needle of the present invention can be manufactured of various types of materials such as metals, ceramics, or plastics common to the injection molding process.

To cut one or more threads using a needle of the present invention, one first pulls on its threaded thread ends to tension the thread. One then slides an eye portion of the needle to a location along the threaded thread, and presses edge 17 against the tensioned thread, cutting the thread.

In difficult-to-reach areas of a sewing project between its two backings, one initially pushes the needle through a first penetration point of the backing into a cavity between the two backings One next pulls the needle through the cavity between the backings. One then pushes the needle's tip and elongated portions into view through a second point in the backing. A distance between the two penetration points of the backing establishes a desired length of what will become a hidden thread end. A configuration of this arrangement leaves the eye portion of the needle remaining inside the backing of the project. One then angles the tip portion of the needle toward the first penetration point of the needle, exposing the threaded thread to edge 17. Next, one tensions the thread and pulls the thread against edge 17 and cuts the thread while inside the cavity. Finally, one pulls the eye portion of the needle through the backing and extracts the remaining, cut thread end through the first penetration point of the needle.

Description

Alternate Embodiments

Figure 1B:
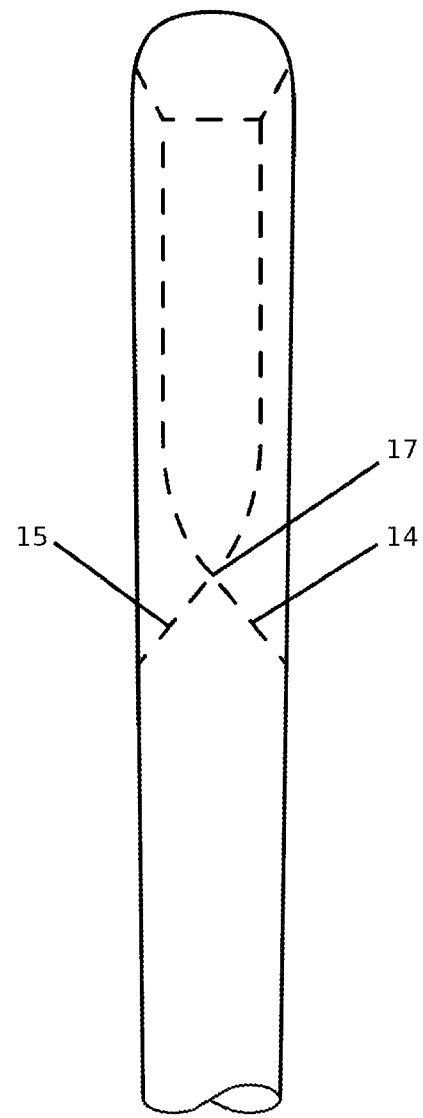

Referring again to FIGS. 1A and 1B, in an alternate embodiment, edge 17 is a non-deburred edge. In yet another alternate embodiment, surfaces 14 and 15 are non-deburred surfaces.

Still another alternate embodiment of the present invention is illustrated in FIGS. 2A (front view) and 2B (side view). A needle has a conventional elongated portion (not shown), a conventional tip portion (not shown) adjacent the elongated portion, and an eye portion adjacent the elongated portion opposite its tip portion, the eye portion having recessed surfaces 25 and 26 intersecting at recessed edge 19 at an angle that creates a cutting edge at edge 19. In an alternate embodiment, edge 19 is a non-deburred edge. In yet another alternate embodiment, surfaces 25 and 26 are non-deburred surfaces.

Operation

Alternate Embodiments

To cut one or more threads using a needle in its alternate embodiment, one pulls on the ends of the thread to tension it. One then pushes recessed edge 19 against the tensioned thread to cut it. To cut the thread using a needle embodiment comprising non-deburred features, one pushes edge 19 against the tensioned thread, and moves the non-deburred features against the thread in a back-and-forth motion to cause the thread to fray and break, cutting the thread.

Conclusion, Ramification, and Scope

According to the present invention, readers will see that the cutting edge needle of this invention can be used to cut one or more threaded objects using its integrated cutting edge. The needle threads and sews like a conventional hand sewing needle, does not impact conventional hand sewing operations, and will not snag the material being sewn when used during conventional hand sewing. The needle can be used to cut items threaded through its eye portion, and in its alternate embodiment the needle can be used to cut items which are not threaded through its eye portion. The threaded object being cut can be cut to any length. The threaded object can be cut close to the face of the material being sewn, leaving little or no visible thread tail remaining. Items that are cut are cut in a controlled manner. Items that are cut can be cut to any desired length inside difficult-to-reach cavities of a sewing project.

The cutting edges of the needle are designed into the surface of the needle in such a way as to minimize the probability of the operator's skin coming in contact with the cutting edge.

The needle simplifies sewing projects by cutting its own threaded objects, thus occasionally eliminating the need for other cutting tools.

The needle is easily manufactured, and its manufacture adds an insignificant unit cost increase to each needle made.

While the above description contains many specifications, these should not be construed as limitations on the scope of the invention, but as exemplifications of the presently preferred embodiments thereof. Many other ramifications and variations are possible within the teachings of the invention.

For example, the preferred embodiment of the invention places the cutting edge at a focus of the eye portion nearest the tip portion of the needle. The cutting edge could be relocated to one or more different edges along the eye portion of the needle, or the eye portion may be comprised of all cutting edges. Its cutting edge could be at the end of a channel or along a channel within or adjacent its eye portion.

The alternate embodiment of the cutting edge needle places the recessed cutting edge at a surface of the eye portion of the needle opposite the tip portion. Its cutting edge could be relocated to a different part of the surface of the needle.

Its cutting edge shape could have a different form. It could be a V shaped trough, it could be slightly curved, or some other shape.

The scope of the background and advantages of the invention target only quilters. The invention could be used in the medical industry for use in suturing.

Thus the scope of the invention should be determined by the appended claims and their legal equivalents, and not by the examples given.

I claim:
1. A cutting edge needle comprising:
   an elongated portion;
   a tip portion attached to the elongated portion; and
   an eye portion attached to the elongated portion, wherein the eye portion comprises a frictionally engageable cutting edge, wherein the frictionally engageable cutting edge (19) is located at the end of the eye portion distal to the tip of the needle, and located outside of the eye of the needle.
2. The cutting edge needle of claim 1, wherein the structure of the needle is monolithic.

* * * * *